(12) United States Patent
Sanders (10) Patent No.: US 11,944,772 B2
(45) Date of Patent: Apr. 2, 2024

(54) WOUND THERAPY SYSTEM WITH HUMIDIFIER

(71) Applicant: KCI Licensing, Inc., San Antonio, TX (US)

(72) Inventor: Teryl Blane Sanders, San Antonio, TX (US)

(73) Assignee: Solventum Intellectual Properties Company, Maplewood, MN (US)

( * ) Notice: Subject to any disclaimer, the term of this patent is extended or adjusted under 35 U.S.C. 154(b) by 85 days.

(21) Appl. No.: 17/606,129

(22) PCT Filed: May 11, 2020

(86) PCT No.: PCT/US2020/032365
§ 371 (c)(1),
(2) Date: Oct. 25, 2021

(87) PCT Pub. No.: WO2020/231936
PCT Pub. Date: Nov. 19, 2020

(65) Prior Publication Data
US 2022/0203016 A1 Jun. 30, 2022

Related U.S. Application Data (60) Provisional application No. 62/847,650, filed on May 14, 2019.

(51) Int. Cl.
*A61M 35/00* (2006.01)
*A61F 13/05* (2024.01)
(Continued)

(52) U.S. Cl.
CPC ............ *A61M 35/30* (2019.05); *A61F 13/05* (2024.01); *A61L 15/425* (2013.01); *A61M 1/73* (2021.05);
(Continued)

(58) Field of Classification Search
CPC .......... A61M 35/30; A61M 2205/3327; A61M 2205/3368; A61F 13/00068
See application file for complete search history.

(56) References Cited

U.S. PATENT DOCUMENTS 1,355,846 A   10/1920   Rannells
2,547,758 A    4/1951   Keeling
(Continued)

FOREIGN PATENT DOCUMENTS

AU   550575 B2   3/1986
AU   745271 B2   3/2002
(Continued)

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.
(Continued)

*Primary Examiner* — Philip R Wiest
*Assistant Examiner* — Matthew Wrubleski (57) ABSTRACT

A wound therapy device includes a wound dressing and a humidifier configured to deliver humid air to a wound site to which the wound dressing is applied. The humidifier may be a remote structure that is fluidly connected to the wound dressing applied about a patient's skin at a wound site. Alternatively, the humidified may be integrated with the wound dressing to define an integral, portable therapy device that may be worn by the patient. The wound therapy device may be a standalone wound treatment device, or may be used in conjunction with other wound treatment devices, such as, e.g., negative pressure wound therapy devices.

18 Claims, 5 Drawing Sheets

(51) Int. Cl.
*A61L 15/42* (2006.01)
*A61M 1/00* (2006.01)
(52) U.S. Cl.
CPC .............. *A61M 1/85* (2021.05); *A61M 1/912* (2021.05); *A61M 1/915* (2021.05); *A61M 1/94* (2021.05); *A61M 1/962* (2021.05); *A61M 1/964* (2021.05); *A61M 2205/05* (2013.01); *A61M 2205/3327* (2013.01); *A61M 2205/3368* (2013.01); *A61M 2205/3553* (2013.01); *A61M 2205/8206* (2013.01)

(56) References Cited

U.S. PATENT DOCUMENTS

| | | | |
|---|---|---|---|
| 2,632,443 A | 3/1953 | Lesher | |
| 2,682,873 A | 7/1954 | Evans et al. | |
| 2,910,763 A | 11/1959 | Lauterbach | |
| 2,969,057 A | 1/1961 | Simmons | |
| 3,066,672 A | 12/1962 | Crosby, Jr. et al. | |
| 3,367,332 A | 2/1968 | Groves | |
| 3,520,300 A | 7/1970 | Flower, Jr. | |
| 3,568,675 A | 3/1971 | Harvey | |
| 3,648,692 A | 3/1972 | Wheeler | |
| 3,682,180 A | 8/1972 | McFarlane | |
| 3,826,254 A | 7/1974 | Mellor | |
| 4,080,970 A | 3/1978 | Miller | |
| 4,096,853 A | 6/1978 | Weigand | |
| 4,139,004 A | 2/1979 | Gonzalez, Jr. | |
| 4,165,748 A | 8/1979 | Johnson | |
| 4,184,510 A | 1/1980 | Murry et al. | |
| 4,233,969 A | 11/1980 | Lock et al. | |
| 4,245,630 A | 1/1981 | Lloyd et al. | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,465,485 A | 8/1984 | Kashmer et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielsen | |
| 4,640,688 A | 2/1987 | Hauser | |
| 4,655,754 A | 4/1987 | Richmond et al. | |
| 4,664,662 A | 5/1987 | Webster | |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt | |
| 4,941,882 A | 7/1990 | Ward et al. | |
| 4,953,565 A | 9/1990 | Tachibana et al. | |
| 4,969,880 A | 11/1990 | Zamierowski | |
| 4,985,019 A | 1/1991 | Michelson | |
| 5,037,397 A | 8/1991 | Kalt et al. | |
| 5,086,170 A | 2/1992 | Luheshi et al. | |
| 5,092,858 A | 3/1992 | Benson et al. | |
| 5,100,396 A | 3/1992 | Zamierowski | |
| 5,134,994 A | 8/1992 | Say | |
| 5,149,331 A | 9/1992 | Ferdman et al. | |
| 5,167,613 A | 12/1992 | Karami et al. | |
| 5,176,663 A | 1/1993 | Svedman et al. | |
| 5,215,522 A | 6/1993 | Page et al. | |
| 5,232,453 A | 8/1993 | Plass et al. | |
| 5,261,893 A | 11/1993 | Zamierowski | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,342,376 A | 8/1994 | Ruff | |
| 5,344,415 A | 9/1994 | DeBusk et al. | |
| 5,358,494 A | 10/1994 | Svedman | |
| 5,383,447 A * | 1/1995 | Lang .................. | A61M 16/1085 128/201.13 |
| 5,437,622 A | 8/1995 | Carion | |
| 5,437,651 A | 8/1995 | Todd et al. | |
| 5,527,293 A | 6/1996 | Zamierowski | |
| 5,549,584 A | 8/1996 | Gross | |
| 5,556,375 A | 9/1996 | Ewall | |
| 5,607,388 A | 3/1997 | Ewall | |
| 5,636,643 A | 6/1997 | Argenta et al. | |
| 5,645,081 A | 7/1997 | Argenta et al. | |
| 6,071,267 A | 6/2000 | Zamierowski | |
| 6,135,116 A | 10/2000 | Vogel et al. | |
| 6,241,747 B1 | 6/2001 | Ruff | |
| 6,287,316 B1 | 9/2001 | Agarwal et al. | |
| 6,345,623 B1 | 2/2002 | Heaton et al. | |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,814,079 B2 | 11/2004 | Heaton et al. | |
| 7,846,141 B2 | 12/2010 | Weston | |
| 8,062,273 B2 | 11/2011 | Weston | |
| 8,216,198 B2 | 7/2012 | Heagle et al. | |
| 8,251,979 B2 | 8/2012 | Malhi | |
| 8,257,327 B2 | 9/2012 | Blott et al. | |
| 8,398,614 B2 | 3/2013 | Blott et al. | |
| 8,449,509 B2 | 5/2013 | Weston | |
| 8,529,548 B2 | 9/2013 | Blott et al. | |
| 8,535,296 B2 | 9/2013 | Blott et al. | |
| 8,551,060 B2 | 10/2013 | Schuessler et al. | |
| 8,568,386 B2 | 10/2013 | Malhi | |
| 8,679,081 B2 | 3/2014 | Heagle et al. | |
| 8,834,451 B2 | 9/2014 | Blott et al. | |
| 8,926,592 B2 | 1/2015 | Blott et al. | |
| 9,017,302 B2 | 4/2015 | Vitaris et al. | |
| 9,198,801 B2 | 12/2015 | Weston | |
| 9,211,365 B2 | 12/2015 | Weston | |
| 9,289,542 B2 | 3/2016 | Blott et al. | |
| 10,300,180 B1 | 5/2019 | Quisenberry et al. | |
| 2002/0077661 A1 | 6/2002 | Saadat | |
| 2002/0115951 A1 | 8/2002 | Norstrem et al. | |
| 2002/0120185 A1 | 8/2002 | Johnson | |
| 2002/0143286 A1 | 10/2002 | Tumey | |
| 2004/0074493 A1 * | 4/2004 | Seakins ............. | A61M 16/1095 128/203.16 |
| 2006/0124127 A1 * | 6/2006 | Du ..................... | A61M 16/145 128/201.13 |
| 2007/0118096 A1 | 5/2007 | Smith et al. | |
| 2011/0034861 A1 | 2/2011 | Schaefer | |
| 2011/0130712 A1 * | 6/2011 | Topaz ............... | A61F 13/00068 604/23 |
| 2013/0096516 A1 | 4/2013 | Schaefer | |
| 2014/0163491 A1 | 6/2014 | Schuessler et al. | |
| 2015/0027443 A1 * | 1/2015 | Barr ..................... | A61M 16/16 128/203.12 |
| 2015/0080788 A1 | 3/2015 | Blott et al. | |
| 2015/0100045 A1 * | 4/2015 | Allen .................... | A61M 1/96 604/543 |
| 2016/0030722 A1 | 2/2016 | Anderson et al. | |
| 2016/0354535 A1 * | 12/2016 | Blott .................... | A61N 5/025 |
| 2017/0000968 A1 * | 1/2017 | Harrington ......... | A61M 16/026 |

(56) References Cited

U.S. PATENT DOCUMENTS

| | | | |
|---|---|---|---|
| 2017/0143931 A1* | 5/2017 | Zheng | A61M 16/164 |
| 2018/0143442 A1* | 5/2018 | Gupta | A61M 21/00 |
| 2018/0263835 A1* | 9/2018 | Eswara | A61G 10/02 |

FOREIGN PATENT DOCUMENTS

| | | |
|---|---|---|
| AU | 755496 B2 | 12/2002 |
| CA | 2005436 A1 | 6/1990 |
| CN | 102049069 B | 10/2012 |
| DE | 26 40 413 A1 | 3/1978 |
| DE | 43 06 478 A1 | 9/1994 |
| DE | 29 504 378 U1 | 9/1995 |
| DE | 102013008964 A1 | 11/2014 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 A | 6/1953 |
| GB | 2195255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/20041 A1 | 9/1994 |
| WO | 96/05873 A1 | 2/1996 |
| WO | 97/18007 A1 | 5/1997 |
| WO | 99/13793 A1 | 3/1999 |

OTHER PUBLICATIONS

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, MD., et al.; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; dated Nov. 23, 1995.

PCT International Search Report for PCT International Application PCT/GB98/02713; dated Jan. 8, 1999.

PCT Written Opinion; PCT International Application PCT/GB98/02713; dated Jun. 8, 1999.

PCT International Examination and Search Report, PCT International Application PCT/GB96/02802; dated Jan. 15, 1998 & Apr. 29, 1997.

PCT Written Opinion, PCT International Application PCT/GB96/02802; dated Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu.N., et al; "Active Wound Drainage", Vestnki Khirurgi, vol. 138, Issue 4, 1987, and 7 page English translation thereof.

Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.

Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.

N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, "The Use of Hypermia in the Postoperative Treatment of Lesions of the Extremities and Thorax,"Journal of the American Medical Association 64 (1915), pp. 1548-1549.

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, (56) References Cited

OTHER PUBLICATIONS editor-in-chief Prov. V.I. Parahonyak (S.M. Kirov Gorky State Medical Institute, Gorky, U.S.S.R. 1987) ("Solovev Guidelines").

V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C. @ Therapy Clinical Guidelines: A Reference Source for Clinicians; Jul. 2007.

International Search Report and Written Opinion for Corresponding Application No. PCT/US2020/032365 dated Sep. 11, 2020.

\* cited by examiner

WOUND THERAPY SYSTEM WITH HUMIDIFIER

CROSS-REFERENCE TO RELATED APPLICATIONS

This application claims the benefit of priority to U.S. Provisional Application No. 62/847,650, filed on May 14, 2019, which is incorporated herein by reference in its entirety.

BACKGROUND

Maintaining a moist wound site environment is known to be advantageous during wound healing. Application and maintenance of negative pressure to a wound site is also known to be advantageous to wound healing. In certain existing wound treatment systems configured to maintain a wound site moist during treatment, a quantity of fluid (i.e. liquid) is instilled to a space defined between the wound site and a lower surface of a wound dressing that is attached about the wound site. Such systems have demonstrated further advantages over moist wound healing and negative pressure therapy alone. The instilled fluid is typically configured to be kept at the wound site for a predetermined dwell time, following which non-absorbed and/or non-evaporated fluid may be removed from the wound site by applying negative pressure to the wound site.

Despite the benefits of existing therapy systems, it would be desirable to provide a system that provides the benefit of maximizing moisture at a wound site, without requiring liquid to be introduced to the wound site, and without requiring the use of the system with a separate NWT system.

SUMMARY

In one implementation of the present disclosure, a wound therapy device includes a wound dressing and a humidifier. The humidifier is configured to deliver humid air to a wound site to which the wound dressing is applied.

The wound therapy device may be a standalone therapy device. In some instances, the humidifier is supported atop an upper surface of the wound dressing. In other embodiments, the humidifier may be discrete from and located remote from the wound dressing.

The wound therapy device may include a sensing element configured to detect humidity at the wound site to which the wound dressing is applied. A controller may be configured to control operation of the humidifier. In some embodiments, the controller may be configured to control operation of the humidifier in response to the humidity at the wound site detected by the sensing element. As an example, the controller may be configured to operate the humidifier in response to the sensing element detecting a degree of humidity at the wound site that is below a predetermined threshold.

The humidifier may include a fluid reservoir. In some instances, two or more different fluids are provided within the fluid reservoir. At least one of the fluids may be a medicament. Also, the humidifier may include a moisture generating element. The moisture generating element may include a heater. The moisture generating element may also include a piezoelectric transducer. In some instances, the moisture generating element may include a wick. In yet other embodiments, the moisture generating element may include an impeller. The moisture generating element may include a heat moisture exchanger. For example, the moisture generating element may include an active heat and moisture exchanger. As another example, the moisture generating element may include a hygroscopic heat and moisture exchanger. In yet other instances, the moisture generating element may include an atomizer.

The humidifier may further include a pump configured to deliver humid air generated by the humidifier to the wound site. Also, the humidifier may include a power source. In some embodiments, a fluid tube extends between and fluidly connects the humidifier and the wound dressing. An interior of the fluid tube may be insulated to prevent condensation. For example, an interior of the fluid tube may be coated with an anti-condensate material.

A controller may be configured to initiate and cease operation of the humidifier at predetermined intervals. Furthermore, the controller may be configured to operate the humidifier based on ambient humidity. In some instances, a heating element may be configured to heat the humid air to a desired temperature prior to delivering the humid air to the wound site.

In some embodiments, a scaffold structure may be located between the wound dressing and the humidifier. In some instances, the scaffold may be configured to promote condensation of the humid air generated by the humidifier into droplets. Also, the scaffold may be arranged relative to the wound dressing such the droplets formed on the scaffold are allowed to drip to the wound site. Furthermore, the location of the scaffold relative to the wound dressing may be selected based on a desired drip rate.

The wound dressing may be a bolster dressing. In some embodiments, the wound dressing includes an absorbent layer. Furthermore, the wound dressing may include a foam layer. Additionally, the wound dressing may include a porous layer.

In some embodiments, the wound dressing is operably connected to a negative pressure wound therapy (NPWT) device configured to evacuate air from the wound site. A fluid tube may extend between and fluidly connects the wound dressing and the humidifier. A fluid tube may also extend between and fluidly connect the wound dressing and a NPWT device. In some instances, the fluid tube that fluidly connects the wound dressing and the NPWT device is the same fluid tube that fluidly connects the wound dressing and the humidifier. In other instances, the fluid tube that fluidly connects the wound dressing and the NPWT device may be different than the fluid tube that fluidly connects the wound dressing and the humidifier. In some embodiments, the fluid tube that fluidly connects the wound dressing and the NPWT device and the fluid tube that fluidly connects the wound dressing and the humidifier may be attached to one another to form an integral tubing element.

In one implementation of the present disclosure, a method of treating a wound includes applying a wound dressing to a wound site. The wound dressing is fluidly connected to a humidifier. The humidifier is operated to generate humid air. The humid air from the humidifier is delivered to the wound site.

The humidifier is operated in response to a measured humidity. The measured humidity may correspond to a degree of humidity detected in the ambient environment. Furthermore, the measured humidity may also correspond to a degree of humidity detected at the wound site. A controller may be configured to operate the humidifier in response to the measured humidity being below a predetermined threshold level.

Humid air may be delivered to the wound site in response to the operation of a pump. The operation of the pump may be configured to transfer the humid air generated by the humidifier to the wound dressing via a fluid tube extending between and fluidly connecting the humidifier and the wound dressing. In some embodiments, an interior of the fluid tube may be insulated to prevent condensation. For example, an interior of the fluid tube may be coated with an anti-condensate material.

In some embodiments, operation of the humidifier may be initiated and stopped according to predetermined intervals. Also, the operation of the humidifier may be initiated by a controller in response to a degree of humidity detected by a hygrometer supported by the wound dressing.

Humid air is heated prior to delivering the humid air to the wound site. Also, the humid air may be condensed into droplets at a location proximate the wound dressing. Furthermore, a pump fluidly connected to the wound dressing may be operated to evacuate air from the wound site.

Those skilled in the art will appreciate that the summary is illustrative only and is not intended to be in any way limiting. Other aspects, inventive features, and advantages of the devices and/or processes described herein, as defined solely by the claims, will become apparent in the detailed description set forth herein and taken in conjunction with the accompanying drawings.

DETAILED DESCRIPTION

Referring generally to the FIGURES, a humidification system and method of its use are disclosed according to various exemplary embodiments. As will be described in more detail below, the humidification system described herein is advantageously configured to promote the healing of a wound by maintaining the wound site moist, while also minimizing the risk of leakage of the system. Additionally, the humidification system may be used as a standalone treatment, without requiring the use of any additional treatment systems to provide the desired treatment of the wound. Accordingly, such humidification systems may advantageously be used in non-acute, or home-care settings.

Figure 1A:
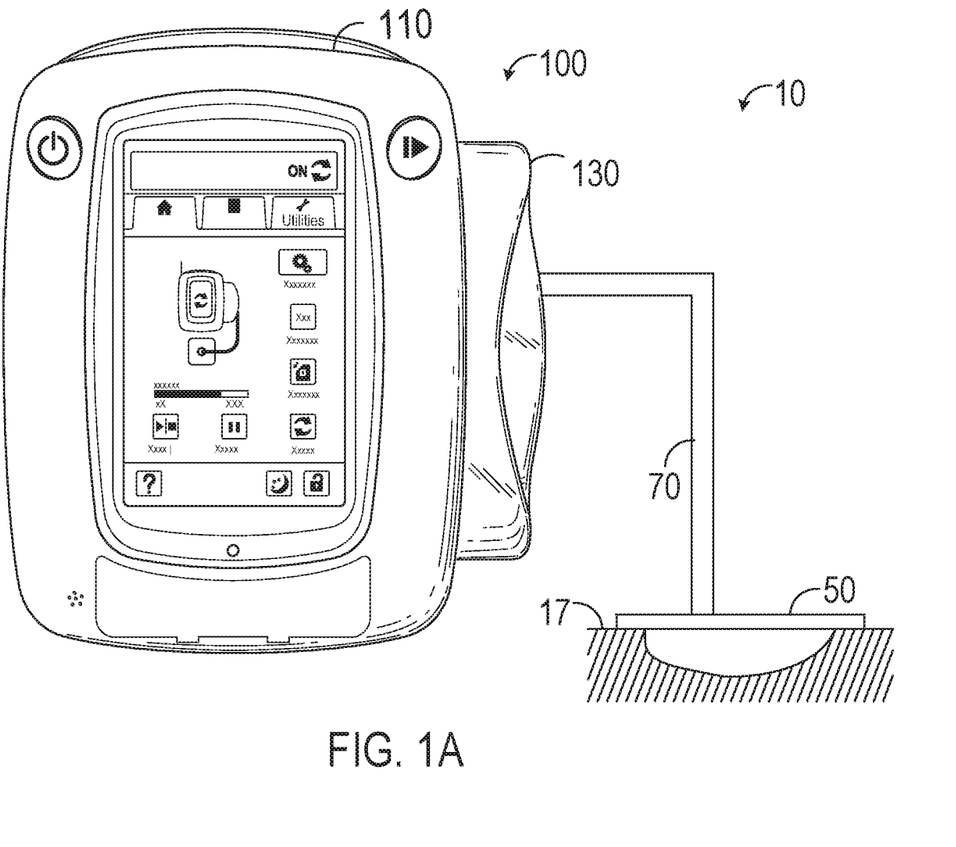
FIG. 1A illustrates a humidification system comprising a wound dressing and remotely located humidification unit, according to an exemplary embodiment.
Figure 1B:
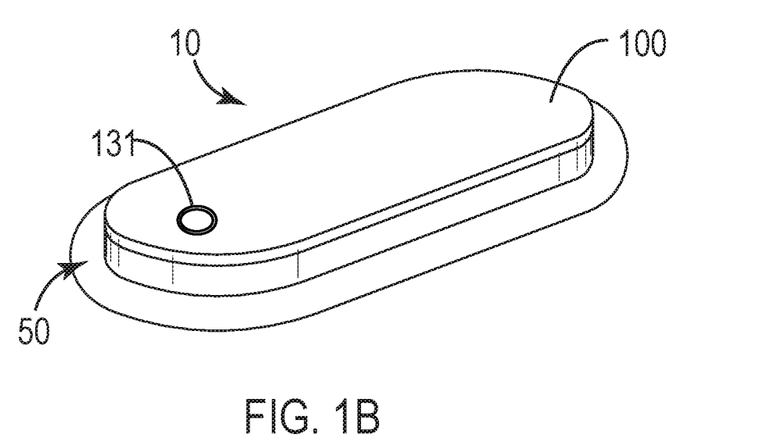
FIG. 1B illustrates a humidification system comprising an integrally attached wound dressing and humidification unit, according to an exemplary embodiment.

As shown in the representative block diagrams of FIGS. 1A and 1B, a humidification system 10 includes a wound dressing 50 configured to be sealed about a wound 15 to be treated, and a humidification unit 100 fluidly connected to the wound dressing 50 and configured to deliver humidified air to a wound treatment space 20 defined between the wound dressing 50 and the wound 15 about which the wound dressing 50 is applied. As will be described in more detail below, the humidification unit 100 generally includes a moisture generating element 110 and a fluid reservoir 130 configured to store a source of fluid. It should be understood that the term fluid includes any liquids that are suitable for humidification, including liquids with added elements (e.g. active elements, medicaments, etc.) for comfort or therapeutic purposes, and that humidified fluid includes fluid that has been converted to gas, gaseous, vapor, droplet, mist, aerosolized, etc. form.

Referring to FIG. 1A, in some embodiments the wound dressing 50 and humidification 100 unit may be formed as separate, discrete elements that are located remote from one another. In such embodiments, the wound dressing 50 and humidification unit 100 may be fluidly connected via a fluid tubing 70 extending between the wound dressing 50 and the humidification unit 100. In some such embodiments, the humidification unit 100 may be located remote from the patient. In other such embodiments, the humidification unit 100 may alternatively be configured to be worn or otherwise supported by a patient during use, thereby defining a portable and optionally wearable humidification system 10.

In other embodiments, such as representatively illustrated by the embodiment of FIG. 1B, the humidification system 10 may be defined by an arrangement in which some or all of the humidification unit 100 is supported by the wound dressing 50. As shown in FIG. 1B, according to some embodiments, the entirety of the humidification unit 100 may advantageously be supported by the wound dressing 50, so as to define an integral, self-contained system that may be easily and discretely worn by a patient during use. As shown in FIG. 1B, according to various such embodiments, the entirety of the humidification unit 100 may be located underneath a backing layer 51 of the wound dressing 50. Alternatively, in other embodiments, a portion of, or the entirety of, the humidification unit 100 may be supported on top of the wound dressing 50.

As illustrated by FIGS. 1A and 1B, according to various embodiments, the humidification system 10 may define a standalone system configured to be operated independently from any other wound treatment devices or systems. In other embodiments, such as representatively illustrated by FIGS. 2A and 2B, the humidification system may optionally also be used with any type and number of additional treatment systems 30 including, but not limited to: NPWT systems; closed negative pressure surgical systems; graft bolstering systems; fluid instillation systems; incision closure systems; topical oxygen wound systems; debridement systems, etc. Representative, non-limiting examples of various additional system with which the humidification system may be used include, e.g., PREVENA™ Therapy Systems, NANOVA™ Therapy Systems, SNAP™ Therapy Systems, V.A.C.® Therapy Systems, etc., each of which is available from KCl LICENSING, INC.

Figure 2A:
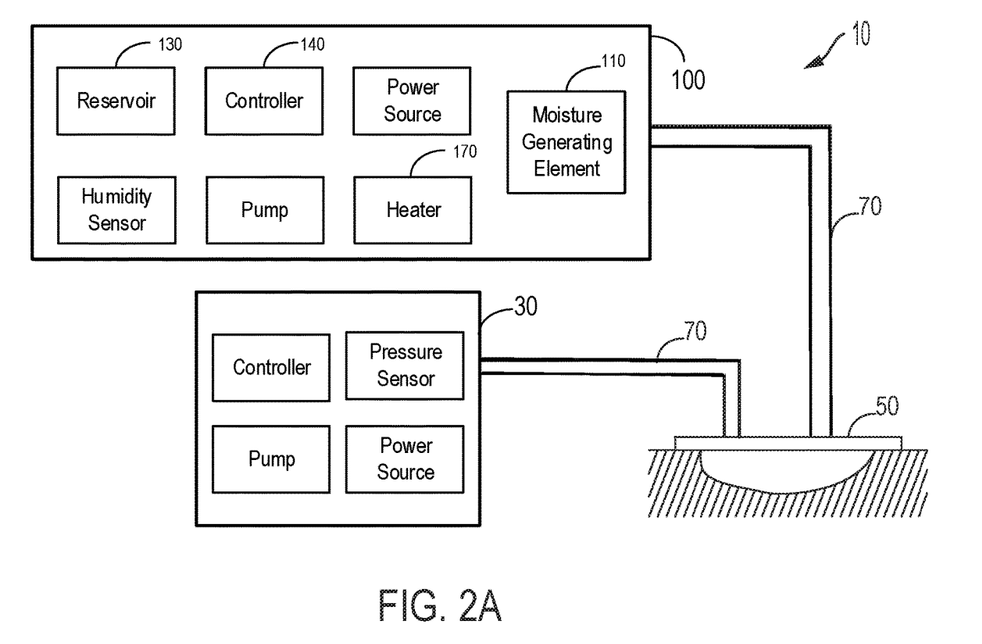
FIG. 2A illustrates a combined wound therapy system including a humidification system and a remotely located additional treatment system, according to an exemplary embodiment.
Figure 2B:
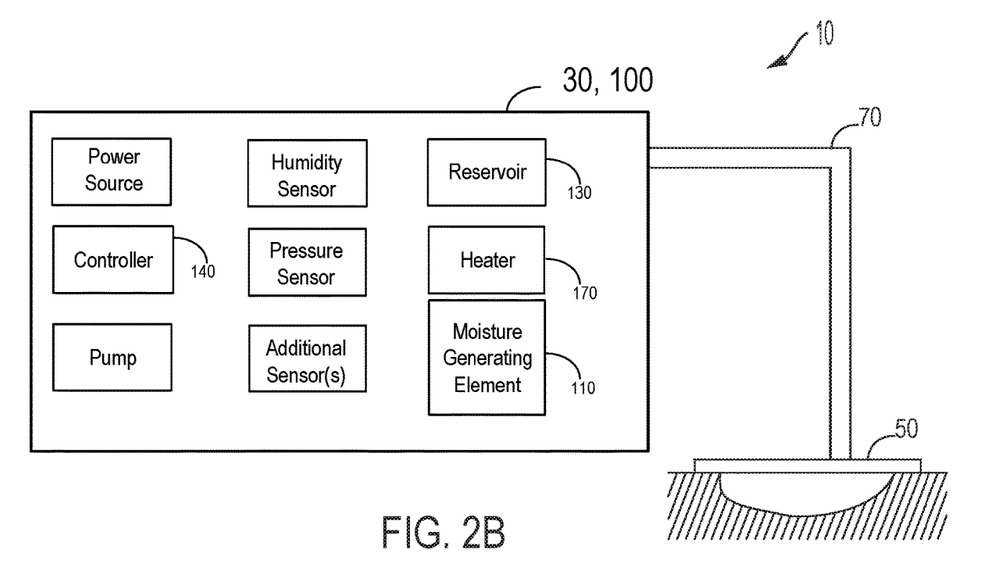
FIG. 2B illustrates a combined wound therapy system including a humidification system and an integrally incorporated additional treatment system, according to an exemplary embodiment.

As illustrated by FIGS. 2A and 2B, in embodiments in which the humidification system 10 is used with an additional treatment system 30, the humidification system 10 may be integrated with the additional treatment system 30 according to varying degrees. For example, as shown representatively by FIG. 2A, in some embodiments the humidification system 10 and additional treatment system 30 may be provided as entirely separate systems that are each operably attached to a common wound dressing 50. Referring to FIG. 2B, according to other embodiments; the humidification system 10 may alternatively be entirely or partially integrated and incorporated into the additional treatment system 30, or vice versa. In some such embodiments, the humidification system 10 and additional treatment system 30 may optionally share components common to both systems. Alternatively, each of the humidification system 10 and additional treatment system 30 may be formed as discrete systems that are integrated into a combined treatment unit.

In embodiments in which the humidification system 10 is used in conjunction with an additional treatment system 30, the humidification system 10 may be used simultaneously with and/or at differing intervals from the use of the additional treatment system 30 over a part of, or the entirety of, the treatment of the wound 15. In some such embodiments, the humidification system 10 and additional treatment system 30 may optionally be separated once treatment using one or both of the systems has been completed.

a. Wound Dressing

The humidification system 10 may include any number of, and combination of, different types of wound dressings 50. In some such embodiments, the wound dressing 50 may exclusively comprise a backing 51 layer configured to be sealed about the patient's skin 17 surrounding the wound 15 so as to define a treatment space 20 between the wound dressing 50 and the wound 15 which the humidified air is intended to treat. Alternatively, in other embodiments, the wound dressing 50 may include one or more additional elements, such as, e.g., a foam layer, an absorbent layer, an absorbable matrix, a wound interface layer etc. that may be supported beneath the backing layer 51 of the wound dressing 50. Non-limiting examples of wound dressings that may be used in such self-contained, closed-system humidification system embodiments include any number of advanced wound dressings including, but not limited to, TIELLE™ Dressings, NU-DERM™ Dressings, ADAPTIC™ Dressings, etc., each of which are available from SYSTAGENIX WOUND MANAGEMENT LTD.

For example, as representatively illustrated by FIGS. 3A-3E, according to various embodiments, the wound dressing 50 may include a hydrophobic and/or hydrophilic porous foam pad 59 defining a manifold via which fluids provided to (e.g. humidified air generated by the humidification unit 100) and/or removed from (e.g. exudates and/or air evacuated by an optionally provided NPWT system) the wound 15 may be distributed within the treatment space 20. Non-limiting examples of materials that may be used for such a foam pad 59 include, but are not limited to, a GranuFoam® dressing and/or a WhiteFoam® dressing, each available from Kinetic Concepts, Inc. of San Antonio, Tex.

As will e understood, the wound dressing 50 may be configured to be attached to the skin 17 so as to surround the wound 15 using any one or more attachment structures, such as, e.g. an adhesive provided about at least a portion of a perimeter of the lower surface of the backing layer 51 and/or other layers forming the wound dressing 50. As will also be understood, in embodiments in which the wound dressing 50 includes one or more layers in addition to the backing layer 51, the backing layer 51 and some or all of the one or more layers may be provided as an integrated structure, or may be provided as a plurality of structures that may subsequently be attached about the wound 15. As shown in FIG. 1B, in embodiments in which the humidification system 10 is provided as a single, integrated unit in which the fluid reservoir 130 of the humidification unit 100 is positioned underneath the backing layer 51, a fill port 131 via which the fluid reservoir 130 may be refilled during use of the humidification system 10 may optionally be provided on the backing layer 51

Referring to FIGS. 3A-3E, in embodiments in which the wound dressing 50 and all or a portion of the humidification unit 100 are provided as separate components, the backing layer 51 of the wound dressing may be provided with one or more openings in the backing layer 51 via which the humidification unit 100 may be fluidly coupled with the treatment space 20 defined underneath the backing layer 51. According to some embodiments, connector ports 55 attached along an upper surface and/or lower surface the backing layer 51 may be optionally be provided about the openings to facilitate coupling of the humidification unit 100 to the wound dressing 50.

Figure 3A:
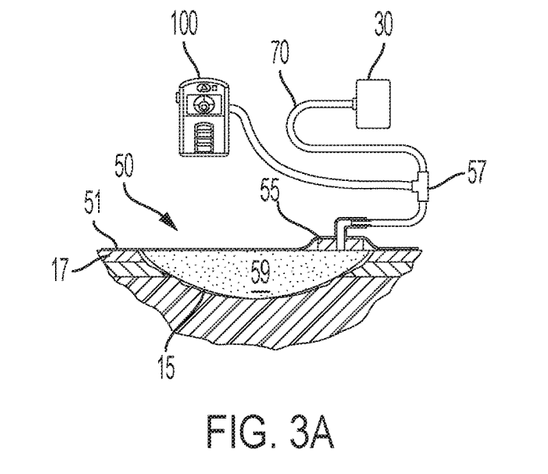
FIGS. 3A-3E illustrate arrangements via which a humidification system and an additional treatment system defining a combined wound therapy system may each be fluidly connected to a wound dressing, according to various exemplary embodiments.
Figure 3B:
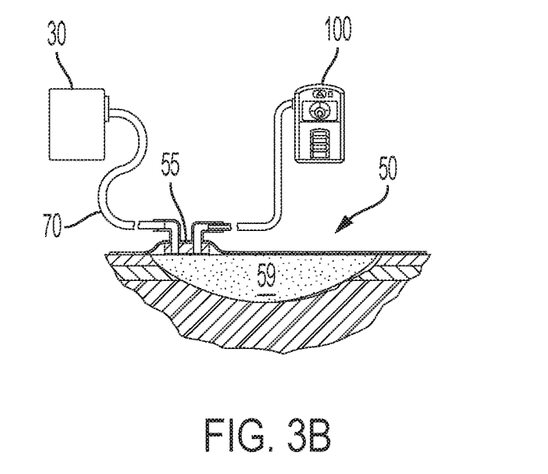

As shown in FIGS. 3A and 3B, according to some embodiments in which the humidification system 10 is used with an additional treatment system(s) 30, the wound dressing 50 may be provided with a single opening (and optional connector port 55) via which each of the humidification unit 100 and additional treatment system 30 communicate with the treatment space 20. As illustrated in FIG. 3A, in some such embodiments, a valve or other switching element 57 may optionally be provided at the connector port 55 and/or upstream of the opening in the backing layer 51 that is configured to selectively fluidly connect one or both of the humidification unit 100 and/or the additional treatment system 30 to the treatment space 20. As illustrated by FIG. 3B, in other such embodiments, the connector port 55 may optionally be formed having two or more fluid attachments, such that the humidification unit 100 and additional treatment system(s) 30 may each be discretely attached to the connector port 55.

Figure 3C:
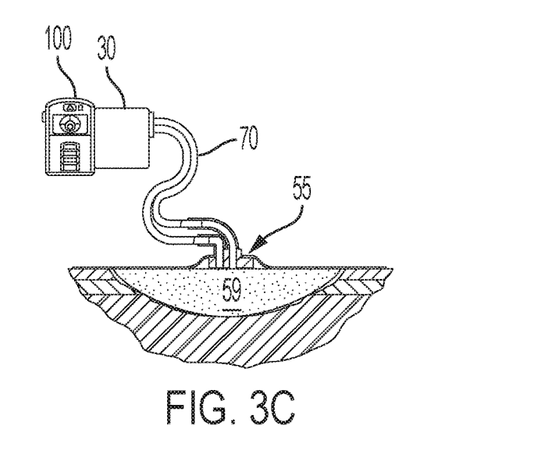
Figure 3D:
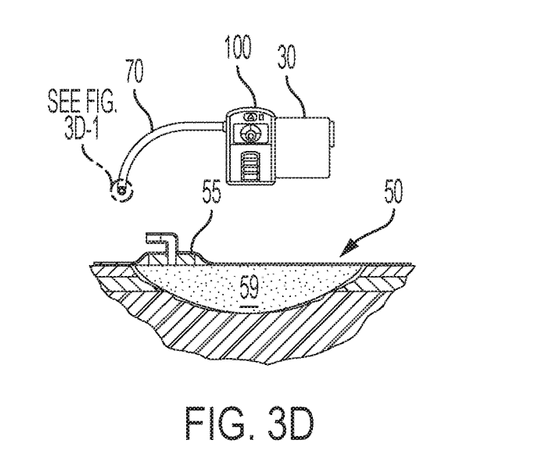
Figure 3D:
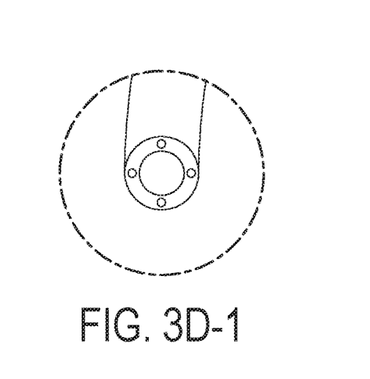

Turning to FIGS. 3C and 3D, in other such embodiments in which the humidification unit 100 and at least one additional treatment system 30 are fluidly connected to a common fluid opening or connector port 55, the humidification unit 100 and treatment system(s) 30 may be connected to the wound dressing 50 via a single, shared tubing element 70 formed with two or more coaxially and/or co-extensively extending separate lumens that provide distinct fluid paths via which the humidification system 100 and additional wound treatment system(s) 30 may fluidly communicate with the wound treatment space 20. As shown in FIG. 3C, in some such embodiments, some or all of the distinct lumens of the tubing element 70 may be configured to be fluidly coupled to distinct fluid openings defined in the backing layer 51, either directly, or via one or more distinct lumens defined by a port 55 supported about the opening on the wound dressing 50. Alternatively, as shown in FIG. 3D, in other embodiments, some or all of the distinct lumens defining the tubing element 70 may instead be fluidly coupled to the wound dressing 50 at a common fluid opening defined by the backing layer 51 (about which a port 55 may be provided).

Figure 3E:
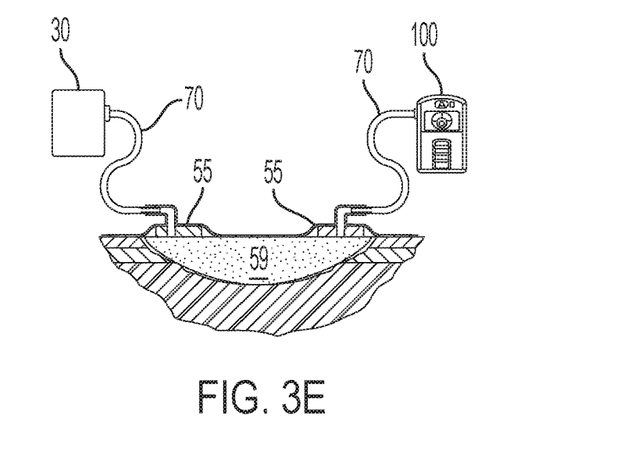

As illustrated in FIG. 3E, according to yet other embodiments, the wound dressing 50 may be provided with a plurality of discrete openings (about which ports 55 may be formed), such that the humidification unit 100 and additional treatment system(s) 30 may each optionally be connected to discrete openings (and optional ports 55) provided in the backing layer 51.

b. Humidification Unit

As illustrated in FIG. 1A, according to some embodiments, the humidification unit 100 (and optionally any additional treatment system 30) may be integrated with the wound dressing 50 to define a self-contained, integrated unitary humidification system 10. In some such embodiments, one or both of the fluid reservoir 130 and moisture generating element 110 of the humidification unit 100 may be attached to and supported by an upper surface of a rigid or flexible backing layer 51 of the wound dressing 50. Alternatively, one or both of the fluid reservoir 130 and the moisture generating element 110 of the humidification unit 100 may be positioned and supported below a lower surface (i.e. underneath) the backing layer 51 of the wound dressing 50. As will be understood, according to some such embodiments, some or all of the humidification unit 100 may be configured to be reusable with a new wound dressing 50 following use of the humidification system 10.

The humidification unit 100 generally comprises a moisture generating element 100 and a fluid reservoir 130. According to various embodiments, the fluid reservoir 130 and moisture generating element 110 may be integrated into a single, attached component. Alternatively, in other embodiments, the fluid reservoir 130 may be a discrete component that may be fluidly connected to the moisture generating element 110 via any number of desired fluid connectors and arrangements. The moisture generating element 110 is configured to generate and deliver humidified air to the wound 15. As will be understood, any number of different types of moisture generating elements 110 may be used to define the humidification unit 100.

For example, according to some embodiments, the moisture generating element 110 may comprise a vaporizer including any number of, or combination of, heating elements configured to heat fluid from the fluid reservoir 130 to generate moist air that may be delivered to the wound treatment space 20. As will be understood, the heating element(s) may be arranged according to any number of configurations via which the heating elements may vaporize fluid from the fluid reservoir 130. In some embodiments, the heating element(s) may be placed adjacent to and/or within the fluid reservoir 130. In embodiments in which moisture generating element 110 is provided as a separate and discrete component from the wound dressing 50, the moisture generating element 110 may alternatively, or additionally, be defined by heating element(s) provided in in-line with fluid tubing 70 extending between the humidification unit 100 and the wound dressing 50, with the heating elements being configured to vaporize any liquid fluid flowing within the fluid tubing 70 from the fluid reservoir 130 prior to the fluid reaching the wound treatment space 20.

In other embodiments, the moisture generating element 110 may comprise an impeller humidifier, in which one or more rotating impeller discs are configured to fling fluid droplets from the fluid reservoir 130 at a diffusing screen which breaks down the droplets into a fine mist that is delivered to the wound treatment space 20.

According to some embodiments, the moisture generating element 110 may comprise an ultrasonic element configured to generate a fine mist that is delivered to the wound treatment space 20. As will be understood, in such embodiments, the ultrasonic element may be defined by any number of, or combination of different elements, including an oscillator, such as, e.g. a piezoelectric element, configured to create vibrations in a vibrating element (such as, e.g., a ceramic diaphragm, a vibration mesh defined by a plurality of laser drilled holes, etc.) that is in contact with fluid in the fluid reservoir 130, resulting in the conversion of the fluid in the fluid reservoir 130 into a mist. In yet other embodiments, the moisture generating element 110 may comprise a jet nebulizer or atomizer including a compressor element configured to pass compressed air or oxygen into the fluid in the fluid reservoir 130, with the high velocity of the compressed air directed through the fluid being configured to turn the fluid into a fine mist that may be used to deliver moisture to the wound site.

In some embodiments, the moisture generating element may comprise a heat moisture exchanger element ("HME element") comprising a heat moisture exchanger material (HME material") positioned in fluid communication with each of the wound treatment space 20 and a pump of the HME element. As will be understood, in embodiments in which the humidification system 10 is used with an additional treatment system 30 comprising a NPWT treatment system, the negative pressure source of the NPWT treatment system may be used as the pump of the I-EVIE element.

In use, the pump of the HME element may be operated to alternate between applying negative pressure and positive pressure to the wound treatment space 20. During the application of a vacuum to the wound treatment space 20, warm water vapor carried by the air that is evacuated from the wound 15 is trapped by the HME material. Upon switching to a positive pressure mode, air that is displaced by the pump passes through the HME material prior to reaching the wound treatment space 20, with the water trapped in the HME material being added to the air that is passed to the wound treatment space 20 to increase the moisture within the treatment space 20.

According to various embodiments, the HME element may optionally also comprise one or more filters, membranes or other materials configured to trap, absorb, or otherwise retain any number of undesired particles (e.g. impurities, microorganisms, etc.) as air is forced into and out from the HME material during operation of the pump. In some embodiments the degree of humidified air and/or the temperature of the humidified air provided by the HME element may optionally be increased by including a hygroscopic unit (such that the HME element defines a hygroscopic condenser humidifier) and/or by including additional moisture and/or heat adding elements (to thereby define an active HME element).

In some embodiments, the moisture generating element 110 may comprise a wicking element formed of an absorbent, porous material having a large surface area. When exposed to fluid from the fluid reservoir 130, the wicking element may be configured to distribute fluid from the fluid reservoir 130 substantially evenly across all of the surface area of the wicking element. Evaporation of the fluid retained across the surface of the wicking element is configured to increase the moisture at the wound treatment space 20. According to various embodiments, the wicking element may be formed from any number of different materials, including, e.g., papers, fibers, fabrics, ceramics, polymer matrices, etc.

As will be understood, in moisture generating element 110 embodiments comprising a wicking element, the wicking element may be exposed to the fluid from the fluid reservoir 130 according to any number of arrangements that would allow for the controlled exposure of the wicking element to limited amounts of fluid. For example, the wicking element may comprise a wick connector via which fluid from the fluid reservoir 130 may be transferred to one or more locations about the surface of the wicking element. In other embodiments, limited amounts of fluid may be applied to the wicking element from the fluid reservoir 130 according to any other number of arrangements, such as, e.g. utilizing a misting or spraying device; a pump system calibrated to dispense small quantities of fluid about one or more locations of the surface of the wicking element, etc.

c. Additional Components

According to various embodiments, the humidification system 10 may optionally also include any number of, and combination of, different components in addition to the humidification unit 100 and wound dressing 50. For example, according to some embodiments, the humidification system 10 may include additional elements such as, but not limited to: delivery and dispersal elements, anti-condensation features, one or more sensors, filter elements, a heater, a control system, one or more power sources, networking and/or communications interfaces, etc. As will be understood, in embodiments in which the humidification unit 100 and wound dressing 50 are provided as discrete and separate components that are connected with fluid tubing 70, such additional optionally included one or more components may be provided as a part of one, some, or all of the humidification unit 100, wound dressing 50 and/or fluid tubing 70, according to any desired combinations and configurations.

i. Delivery and Distribution Elements

According to various embodiments, the humidification system 10 may include any number of additional optional elements configured to assist in the delivery and distribution of humidified air and or fluid within the humidification system 10. For example, according to various embodiments, a transfer element, such as, e.g. a fan or pump 75, may be used to enhance the delivery of the humidified air generated by the moisture generating element 110 to the wound treatment space 20 and/or to optionally allow for transfer of fluid from the fluid reservoir 130 to the moisture generating element 110. As will be understood, the incorporation of such a transfer element may be particularly advantageous in embodiments in which the fluid reservoir 130 is remote from the moisture generating element 110 and/or where the moisture generating element 110 is located remotely from the wound dressing 50. According to some embodiments (not shown) a fan or other transfer element may alternatively, or additionally, be optionally provided within the treatment space 20 so as to circulate air within the treatment space 20.

In addition to optionally including a transfer element configured to transfer humidified air from the moisture generating element 110 to the treatment space 20, according to various embodiments, the humidification system 10 may also optionally include one or more dispersal elements configured to fluidly separate an outlet end of the fluid tubing 70 and the treatment space 20 and/or which are located within the treatment space 20 and which are configured to enhance the distribution and/or circulation of humidified air within the wound treatment space 20 and/or to otherwise increase moisture levels within the treatment space 20.

For example, as noted with reference to FIGS. 3A-3E, according to some embodiments, one or more optionally included wound dressing 50 layers, such as, e.g., a foam pad 59, may act as a fluid manifold via which fluids (including, e.g., humidified air delivered from the humidification unit 100) may be distributed within the wound treatment space 20. In other embodiments, the dispersal element may comprise a structure (e.g. a fan or pump) similar to any optionally provided transfer element. In yet other embodiments, the dispersal structure may comprise any other number of, or combination of, manifold or disperser structures, such as, e.g., baffles, screens, scaffolds, nozzles, etc.

Figure 4A:
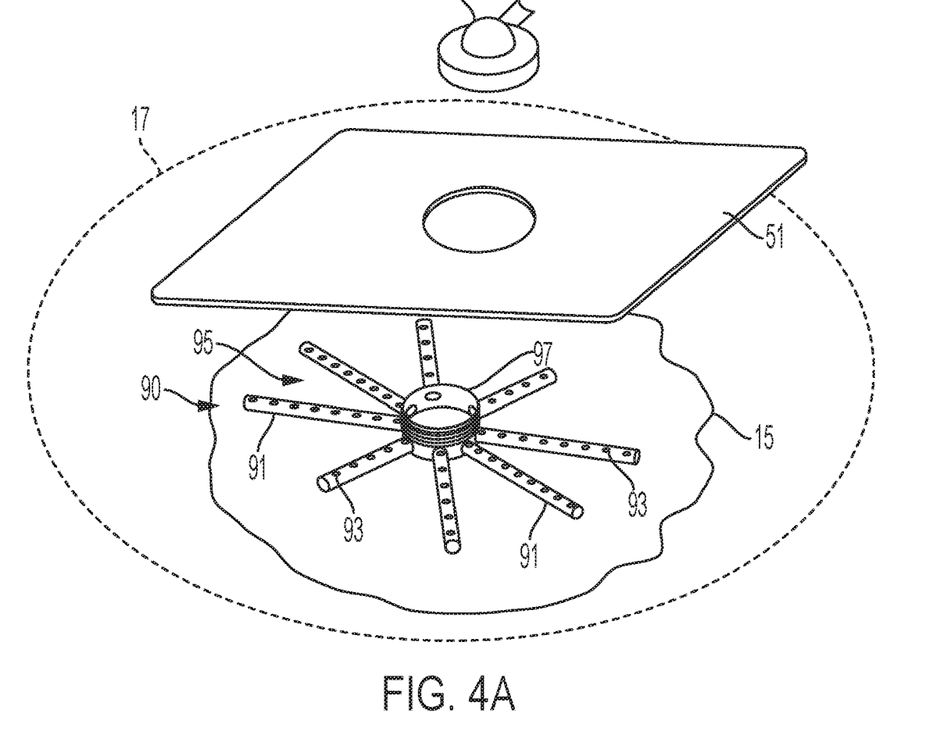
FIGS. 4A-4C illustrate dispersal structures, according to various exemplary embodiments.

As shown in FIG. 4A, according to some embodiments, the dispersal element may optionally be defined by a dispersing surface 91 having an outer perimeter greater than the opening defined by the outlet end of the fluid tubing 70. A plurality of openings 93 are provided about a portion or an entirety of the surface 91 of the dispersal element 90, with humidified air from the fluid tubing 70 being configured to pass through these openings 93 to reach the wound treatment space 20. In some embodiments, the dispersing surface 91 may be provided as a lower surface of a closed housing 95 including a connector 97 via which the dispersal element 90 may be fluidly coupled to the fluid tubing 70. In some such embodiments, the interior of the housing 95 may be hollow, with the humidified air passing into the interior housing 95 through the connector 97 being in fluid communication with each of the openings 93 of the dispersal element 90. Alternatively, in some embodiments, the interior the housing 95 may define a plurality of discrete chambers, with humidified air that passes from the outlet end of the fluid tubing 70 being diverted into a plurality of flow paths defined by the chambers of the housing 95.

Figure 4B:
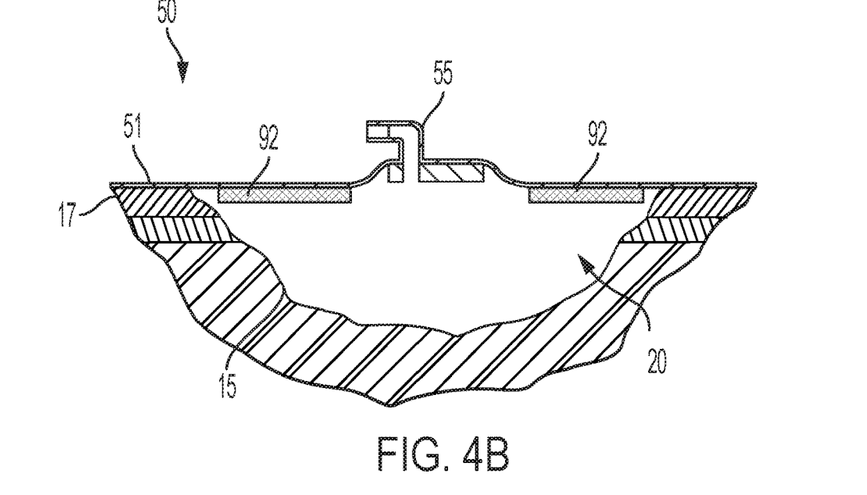

Referring to FIG. 4B, in other embodiments, the dispersal structure may comprise a wicking structure 92 that is supported within the wound treatment space 20. As will be understood, in such embodiments, the wicking structure 92 may be utilized in conjunction with any other one or more moisture generating elements 110 as described herein, with the wicking structure 92 being exposed to humidified air generated using any of the one or more additional moisture generating elements 110 defining the humidification unit 100. According to such embodiments, the wicking structure 92 may optionally be attached to and/or otherwise supported by the backing layer 51, such that the wicking structure 92 is spaced apart from, and optionally not in direct contact with, the wound 15.

Figure 4C:
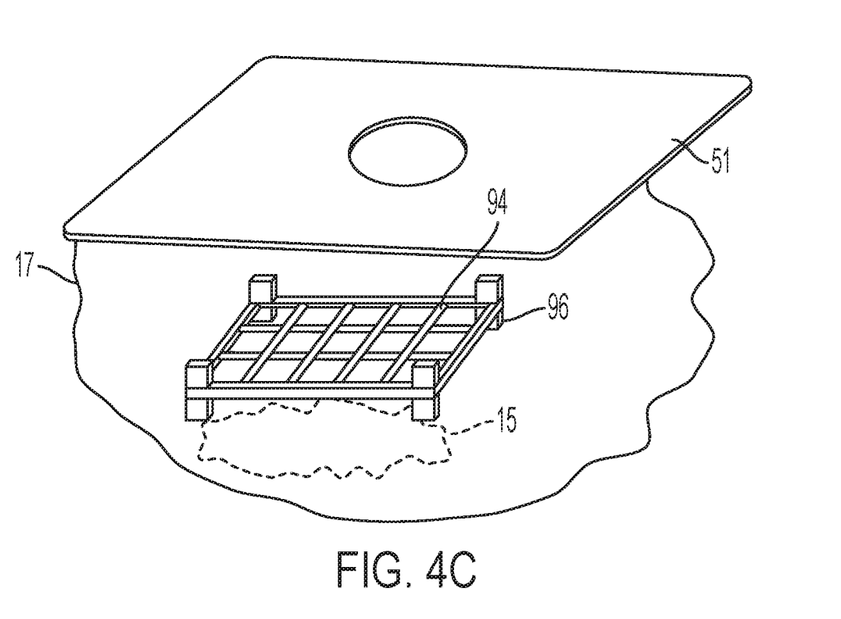

As shown in FIG. 4C, in yet other embodiments, the dispersal structure may optionally comprise a mesh or other scaffold structure 94 defined by a plurality of elongated structures arranged to define a structure having a plurality of openings formed therein. In such embodiments, the mesh or other scaffold structure 94 may be supported by the wound dressing 50 so as to be supported directly opposite from, but spaced apart from, the wound 15. The mesh 94 may be configured to provide a surface area about which humidified air that is delivered to the treatment space 20 may condense, with the condensed moisture particles formed on the scaffold structure 94 being configured to drip onto the wound 15 to thereby provide a gradual, minimal, sustained delivery of fluid to the wound 15. As shown in FIG. 4C, according to some embodiments, a support structure 96 (such as, e.g. strips of foam) may optionally be attached about a lower surface of the scaffold structure 94 and/or an upper surface of the scaffold structure 94, so as to provide a structure via which the mesh structure 94 may be elevated relative to the wound 15 and/or spaced apart from the rear surface of the backing layer 51 when the wound dressing 50 is assembled and attached to a patient's skin 17.

According to various embodiments, it may be desirable to define a large treatment space 20 between the wound 15 and the rear surface of the backing layer 51 (e.g., to allow for a greater volume of humidified air to be delivered to the wound 15, to prevent the backing layer 51 and/or any optionally provided dispersal structures and/or other structures from contacting the wound 15, etc.). As such, in some embodiments (not shown), the wound dressing 50 may comprise a rigid or semi-rigid backing layer 51 that is configured to allow the wound dressing 50 (and optionally any optionally provided dispersal structure(s) or other structure supported thereby) to be supported above and spaced apart from the wound 15. In other embodiments, the wound dressing 50 may alternatively, or additionally, include one or more spacer structures (such as, e.g. the support structures 96 of the wound dressing 50 embodiment of FIG. 4C) via which the backing layer 51 (and any optionally provided dispersal structure(s) or other structure supported thereby) may be elevated relative to the wound 15. As will be understood, in yet other embodiments, any number of, or combination of, other structures and arrangements may be used to optionally support the backing layer 51 in a spaced apart relationship relative to the wound 15.

ii. Anti-Condensation Features

As discussed above according to some embodiments, moisture may be delivered to the wound treatment space 20 in the form of a controlled release of droplets of fluid onto the wound 15. However, in other embodiments, it may be desired to minimize, or entirely prevent, the delivery of fluid in the form of liquid to the wound 15. Instead, it may be desired that fluid be delivered to the wound 15 exclusively, or substantially, as humidified air. Accordingly, in various embodiments, the humidification system 10 may optionally include one or more anti-condensation features.

For example, in some embodiments, the delivery of liquid fluid to the wound 15 may be prevented or minimized by minimizing the length of, or entirely removing, any fluid tubing 70 extending between the moisture generating element 110 and the wound dressing 50. For example, by incorporating the moisture generating element 110 into, on, or adjacent the wound dressing 50, the distance which the humidified air must travel to the wound treatment space 20 may be minimized, thereby decreasing the likelihood of condensation of the humidified air as it travels from moisture generating element 110 to the wound treatment space 20.

In other embodiments, such as, e.g., embodiments in which it is not possible to integrate or otherwise position the moisture generating element 110 within, on or adjacent the wound, it may not be possible (or desirable) to minimize or remove the fluid tubing 70 from the humidification system 10. Accordingly, in some embodiments, the fluid tubing 70 extending between the wound dressing 50 and the humidification unit 100 may optionally include one or more anti-condensation features. For example, in some embodiments, the fluid tubing 70 may be formed having a thick wall and/or may be formed of a material that is configured to minimize the temperature differential between the fluid tubing 70 and the humidified air flowing through the fluid tubing 70. In some embodiments, the fluid tubing 70 may alternatively, or additionally, include an insulating interior and/or exterior coating. In yet other embodiments, the fluid tubing 70 may additionally, or alternatively include any other type of anti-condensate coating provided along a portion of the entirety of the interior lumen of the fluid tubing 70.

In addition, or as an alternative to, the incorporation of anti-condensation features, the fluid tubing 70 may include an absorbent and/or wicking liner provided along all or a part of the interior of the fluid tubing 70. In such embodiments, the absorbent and/or wicking liner may be configured to retain, and optionally remove, any fluid that has condensed along the interior surface of the fluid tubing 70, which may thereby prevent any fluid droplets that have condensed along the interior of the fluid tubing 70 from undesirably seeping into the wound dressing 50.

iii. Heater

As described above, the moisture generating element 110 may be defined according to any number of different configurations and arrangements, and may comprise any number of different elements and components that are configured to allow the moisture generating element 110 to generate humidified air. As also discussed above, not all such moisture generating element 110 embodiments require and/or incorporate a heating element. In some such humidification system 10 embodiments in which the moisture generating element 110 does not include a heating element, the humidification system 10 may optionally be provided with one or more heaters 170 via which the humidified air generated by the moisture generating element 110 and/or the fluid in the fluid reservoir 130 may be heated to a desired temperature. As will be understood, in such embodiments, the optional heater(s) 170 may be incorporated into any or all of the fluid reservoir 130, the moisture generating element 110, the wound dressing 50, the fluid tubing 70, etc. As will also be understood, according to some humidification system 10 embodiments in which the moisture generating element 110 does include one or more heating elements, the humidification system 10 may optionally also include additional heaters 170 via which fluid in the fluid reservoir 130 and/or humidified air in the humidification system 10 may be heated.

iv. Filter Elements

According to various embodiments, one or more filters (e.g. filtration media, UV-light or other sterilization sources, demineralization media etc.) may optionally be provided at one or more various locations about the humidification system 10. For example, according to some embodiments, a filter configured to prevent contamination of the moisture generating element 110 may be provided between the fluid reservoir 130 and the moisture generating element 110. Additionally, or alternatively, a filter configured to remove impurities and/or kill or prevent bacteria or other microorganisms may be provided between the fluid reservoir 130 and the wound treatment space 20. In embodiments in which the wound dressing is fluidly coupled to the fluid reservoir 130 via fluid tubing 70, a filter may optionally be provided along any portion of the fluid tubing 70 between the first end and the second end of the fluid tubing 70.

As will be understood, in embodiments in which the humidification system 10 is incorporated into or otherwise used with an additional treatment system 30, any other number of filters may additionally be incorporated into the humidification system 10. For example, in some embodiments in which the humidification system 10 is used with an additional treatment system 30 comprising a NPWT system, a liquid air separator configured to prevent liquid flow from the wound dressing 50 to the negative pressure source of the NPWT system may be provided anywhere between the wound treatment space 20 and the source of negative pressure, including, e.g., a filter provided underneath the wound dressing 50, at an opening in the backing layer 51 of the wound dressing 50, along a length of fluid tubing 70 extending between the wound dressing 50 and the fluid reservoir 130, at an opening into the fluid reservoir 130, etc.

v. Sensors

According to various embodiments, any number of, and combination of, different sensors may be incorporated into the humidification system 10. Non-limiting examples of the types of various sensors which may be included in the humidification system 10 include: temperature sensors, fluid level sensors; flow rate sensors; pressure sensors, humidity/moisture level sensors; etc. As will be understood, the sensors may be characterized by any number of different structures and may be integrated into the humidification system 10 at any number of different locations so as to be able to detect and monitor conditions any one of, or combination of, the wound treatment space 20, within the fluid reservoir 130, at the moisture generating element 110, within any optionally extending fluid tubing 70 provided between any of the components of the humidification system 10, and/or an external ambient environment. As will be understood, according to various embodiments, readings or other measurements obtained using any or all of the sensors may be communicated with an optionally provided controller 140 of the humidification system and may optionally be used to control operation of the humidification system 10, any optionally provided additional treatment system 30, and/or any other treatment of the wound 15.

vi. Controller

In some embodiments, the humidification system 10 may be configured to be entirely manually operated. Alternatively, in other embodiments, the humidification system 10 may comprise a controller that may be configured to partially or fully automate some or all of the operation of the humidification system 10. According to some such embodiments, the controller may be configured to operate the humidification system 10 according to one or more different settings or modes. Such settings may include, e.g., entirely static operational modes (e.g., modes in which the humidification system 10 is operated continuously or according to predetermined intervals), entirely user-input modes; modes in which the controller is configured to operate the humidification system 10 based on one or more measured or sensed parameters; modes in which the controller is configured to attain a desired setpoint (e.g. a desired moisture level, temperature, etc.), etc. As will be understood, according to various embodiments, the controller may be configured to operate the humidification system 10 based on readings obtained from any or all optionally provided sensors that are incorporated into and provided with the humidification system 10.

For example, in some embodiments, the humidification system may include one or more hygrometers or other moisture measuring sensors that are configured to measure humidity at the wound treatment space 20 and/or the humidity of the ambient environment. In some such embodiments, the controller may be configured to operate the moisture generating element 110 based on a sensed moisture level at the wound treatment space 20 and/or of the ambient environment. For example, the controller may be configured to operate the moisture generating element 110 to maintain a predetermined degree of humidity at the wound treatment space. In other embodiments, the controller may, e.g., be configured to operate the moisture generating element 110 more frequently and/or for longer time intervals in response to sensing that that ambient humidity is below a predetermined threshold. In yet other embodiments, the controller may be configured to operate the humidification system to attain a desired temperature at the wound treatment space 20. According to yet other embodiments, the controller may be configured to operate the moisture generating element 110 and/or any additional wound treatment system(s) 30 according to any other number of, or combination of factors such as, but not limited to: the volume of fluid that has been evaporated or otherwise humidified and delivered to the wound treatment space 20, the temperature at the wound treatment space 20, the flow rate of humidified air from the moisture generating element 110, the overall duration of treatment using the humidification system 10, the pressure at the wound treatment space 20, etc.

CONFIGURATION OF EXEMPLARY EMBODIMENTS

The construction and arrangement of the systems and methods as shown in the various exemplary embodiments are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.). For example, the position of elements can be reversed or otherwise varied and the nature or number of discrete elements or positions can be altered or varied. Accordingly, all such modifications are intended to be included within the scope of the present disclosure. The order or sequence of any process or method steps can be varied or re-sequenced according to alternative embodiments. Other substitutions, modifications, changes, and omissions can be made in the design, operating conditions and arrangement of the exemplary embodiments without departing from the scope of the present disclosure.

I claim:

1. A wound therapy device, comprising:
a wound dressing; and
a humidifier configured to be disposed between a backing layer of the wound dressing and a wound site to which the wound dressing is applied;
a sensor configured to detect humidity at the wound site; and
wherein the humidifier is further configured to deliver humid air to the wound site.

2. The wound therapy device of claim 1, further comprising a controller configured to control operation of the humidifier.

3. The wound therapy device of claim 2, wherein the controller is configured to control operation of the humidifier in response to the humidity at the wound site detected by the sensing element.

4. The wound therapy device of claim 3, wherein the controller is configured to operate the humidifier in response to the sensing element detecting a degree of humidity at the wound site that is below a predetermined threshold.

5. The wound therapy device of claim 1, wherein the humidifier includes a fluid reservoir.

6. The wound therapy device of claim 5, wherein two or more different fluids are provided within the fluid reservoir.

7. The wound therapy device of claim 5, wherein the humidifier further includes a moisture generating element.

8. The wound therapy device of claim 7, wherein the moisture generating element includes a heater.

9. The wound therapy device of claim 7, wherein the moisture generating element includes a piezoelectric transducer.

10. The wound therapy device of claim 7, wherein the moisture generating element includes a wick.

11. The wound therapy device of claim 7, wherein the moisture generating element includes an impeller.

12. The wound therapy device of claim 7, wherein the moisture generating element includes a heat moisture exchanger.

13. The wound therapy device of claim 7, wherein moisture generating element includes an active heat and moisture exchanger.

14. The wound therapy device of claim 7, wherein moisture generating element includes a hygroscopic heat and moisture exchanger.

15. The wound therapy device of claim 7, wherein moisture generating element includes an atomizer.

16. The wound therapy device of claim 1, further comprising a fluid tube extending between and fluidly connecting the humidifier and the wound dressing, wherein one or both of an interior of the fluid tube and an exterior of the fluid tube is insulated to prevent condensation.

17. The wound therapy device of claim 1, further comprising a fluid tube extending between and fluidly connecting the humidifier and the wound dressing, wherein one or both of an interior of the fluid tube and an exterior of the fluid tube is coated with an anti-condensate material.

18. The wound therapy device of claim 1, wherein the dressing comprises:
   a foam pad configured to be disposed at the wound site;
   a backing layer configured to be disposed over the foam pad and sealed to skin surrounding the wound site; and
   a scaffold structure configured to be supported by the foam pad and spaced apart from the wound site, the scaffold structure further configured to condense moisture at the wound site.

* * * * *